(12) United States Patent
Humar et al.

(10) Patent No.: US 7,935,182 B2
(45) Date of Patent: May 3, 2011

(54) SOLUTION FOR WOOD PRESERVATION

(76) Inventors: Miha Humar, Komenda (SI); Stojan Kosmerl, Vrhnika (SI); Franc Pohleven, Ljubljana (SI)

( * ) Notice: Subject to any disclaimer, the term of this patent is extended or adjusted under 35 U.S.C. 154(b) by 802 days.

(21) Appl. No.: 11/687,269

(22) Filed: Mar. 16, 2007

(65) Prior Publication Data

US 2007/0151476 A1  Jul. 5, 2007

Related U.S. Application Data

(63) Continuation of application No. PCT/SI2005/000028, filed on Sep. 16, 2005.

(30) Foreign Application Priority Data

Sep. 17, 2004  (SI) .................................. 200400260

(51) Int. Cl.
  *A01N 59/14*   (2006.01)
  *A01N 59/00*   (2006.01)
  *A01N 59/02*   (2006.01)
  *A01N 59/20*   (2006.01)

(52) U.S. Cl. ....... 106/18.3; 424/405; 424/637; 424/638; 514/643

(58) Field of Classification Search ................. 106/18.3; 424/633, 635, 637, 638, 405; 514/643
See application file for complete search history.

(56) References Cited

U.S. PATENT DOCUMENTS

| 4,857,322 | A | 8/1989 | Goettsche et al. |
| 6,110,263 | A | 8/2000 | Goettsche et al. |
| 6,306,202 | B1 * | 10/2001 | West ............................ 106/18.3 |
| 6,352,583 | B1 | 3/2002 | Goettsche et al. |
| 6,441,016 | B2 * | 8/2002 | Goettsche et al. ............ 514/383 |
| 6,508,869 | B2 * | 1/2003 | Tseng et al. ...................... 106/2 |
| 6,896,908 | B2 * | 5/2005 | Lloyd et al. .................... 424/635 |
| 2005/0118280 | A1 * | 6/2005 | Leach et al. .................. 424/617 |

FOREIGN PATENT DOCUMENTS

| EP | 0542071 |   | 5/1993 |
| EP | 1034903 |   | 9/2000 |
| SU | 571376 | A * | 9/1977 |
| SU | 1017500 | A * | 5/1983 |

* cited by examiner

*Primary Examiner* — Anthony J Green
(74) *Attorney, Agent, or Firm* — Beem Patent Law Firm

(57) ABSTRACT

A solution for wood preservation is suitable for preservation of wood against wood pests (fungi, insects, termites) that increases resistance of wood against biotic and abiotic factors of decay. The solution for wood preservation comprises an aqueous solution of amine, copper salt, boron salt, quaternary ammonium compound, and carboxylic acid. Preferable embodiment is a solution for wood preservation, consisting of ethanolamine, copper (II) sulphate, disodium octaborate tetrahydrate, alkylbenzyldimethyl ammonium chloride, and octanoic acid dissolved in water. This composition may result in improved copper fixation (decreased leaching of active ingredients from wood during weathering) and improved resistance against the most important wood destroying organisms like wood decay fungi, insects and termites.

3 Claims, No Drawings

SOLUTION FOR WOOD PRESERVATION

CROSS-REFERENCE TO RELATED APPLICATIONS

This application is a continuation of international application PCT/SI2005/000028, filed Sep. 16, 2005, and Slovenian application P-200400260, filed Sep. 17, 2004.

FIELD OF INVENTION

The subject of present invention is aqueous solution for wood preservation against wood pests, and to improve resistance of wood against biotic and abiotic factors of decay.

BACKGROUND

Wood is exposed to various biotic and abiotic factors of decay. These processes are necessary and required in the nature, but when wood is used for construction purposes, we would like to slow them down as much as possible. This is can be achieved by using chemical wood preservatives.

Most of the Slovenian and European wood species produces wood that is not resistant against fungi, insects and termites. If we want to use such wood in hazard class 3 (wood above soil, uncovered) or hazard class 4 (soil or water contact), we have to chemically protect it. Proper treatment prolongs lifespan of wood, what results in cheaper maintenance and safety of wooden construction.

Copper effectiveness against wood decay fungi makes it important constituent of wood preservatives for almost 200 years. In recent years, the use of copper compounds for biocidal purposes has increased. The reasons are: copper compounds are relatively safe, development of pathogens has been minimal; pathogens show increased tolerance against organic fungicides after extended period of use, and thirdly increase in government regulations and restrictions (or outright banning) of alternative products due to their toxicological or environmental impacts. However, traditional copper based wood preservatives had an important drawback; copper did not get fixed into wood and was prone to leaching out of wood.

This problem was resolved, by introducing of fixed waterborne preservatives. Heinrich Bruning discovered that normally soluble metal salts could be made insoluble, or fixed inside wood, by addition of large amounts of chromium. Since carcinogenic nature of chromium compounds is well known, most of the European countries intend to ban use of chromium in wood preservatives. Some of them will allow use of chromium preserved wood only for special purposes that are classified as hazard class IV. Use of chromium based wood preservatives will be banned for children playground equipment, garden furniture. Therefore, intense researches are going on in the world laboratories to develop environmentally acceptable solution for copper fixation in wood preservatives.

Ammonia was found very effective copper fixative long time ago, but due to its emissions this formulation newer came into extensive commercial use. Later ammonia was replaced with amines; particularly ethanolamine and triethanolamine were found very effective copper fixative. Commercial wood preservatives on the basis of copper and ethanolamine are available on the market already. However, copper leaching from such treated wood is still 5-10 times higher than leaching from wood treated with classical copper-chromium based preservatives.

Beside problems with copper fixation, use of copper treated wood is limited because of appearance of copper tolerant fungi as well. Therefore co-biocides are introduced to copper-ethanolamine based aqueous solution to increase protection against copper tolerant fungi. Addition of co-biocides is very tricky, as we have to pay attention not to increase copper leaching.

There are several copper based wood preservatives available on the market. In the major part of the countries (Russia, Ukraine, Africa, Asia, and South America) still uses wood preservatives based on copper, chromium and arsenic salts. American wood preservative association introduces abbreviation CCA for such preservatives. In most of these aqueous solutions copper is in the form of copper oxide. Copper in those preservatives served as fungicides, arsenic as insecticide and secondary fungicide and chromium as fixative. These types of preservatives are available under different commercial names such as: (Celcure A, Tanalith C, Ascu-Greensalts, Wolman CCA, OsmoseK33, Langwood.

In the continental part of Europe, arsenic salts are banned for almost 15 years. In order to ensure protection of wood against insects, boron salts were introduced instead. In some of the Scandinavian countries arsenic was replaced by fluorine compounds.

In the USA besides copper-chromium based preservatives other solutions are used as well. One of them consists of copper, arsenic and ammonium acetate. After 1983 part of arsenic was replaced with zinc. Fixation of these preservatives is very simple; most of copper participates after volatilization of ammonia.

In the eighties, there were preservatives consisting of copper, arsenic and ammonia. Due to unpleasant ammonia emissions, workers on the impregnation systems do not want to use it.

However, completely new solution was developed in Wolman. They developed solution consisting of Cu—HDO (copper hydroxyquinolinolate), that is soluble in solutions with pH value above 7, but precipitates in insoluble form if pH decreases below 6. In acidic wood, copper precipitation appears, rapidly after impregnation. Due to high price, and possible carcinogenic effect of hydroxyquinolinolate, USA EPA does not allow registration of this active ingredient.

Nowadays, ethanolamine is a component of several copper based wood preservatives that are available on the market. This includes copper-quaternary ammonium compound, copper dimethyl-dithio-carbamate, and copper azole. In those preservatives, boron, quaternary ammonium compound or azoles are used as cobiocides, and ethanolamine as fixative. However, detailed molar ratios between copper and amine are not known.

DETAILED DESCRIPTION OF THE INVENTION

Solution for wood preservation according to the present invention offers environmentally acceptable protection of wood against most important wood decay fungi, including white rot, brown rot species as well as copper tolerant isolates. Additionally, wood treated with these preservatives has increased resistance against insects (house longhorn Beatle) and termites. On the other this preservative solution does not contain chromium and arsenic.

Copper ensures effectives against most important wood decay fungi, ethanolamine and carboxylic acid ensures proper fixation and quaternary ammonium compound and boron offers protection against insects, termites and copper tolerant fungi.

The composition of solution for wood preservation according to the present invention is optimized using two criteria, after extensive laboratory testing. Those two goals are: to decrease copper leaching and to increase effectiveness against wood destroying organisms (wood decay fungi, insects, and termites).

Wood preservative solution described in this invention is aqueous solution comprising:

a) selected amine,
b) selected copper salt,
c) selected boron salt,
d) selected co-biocide from the group of quaternary ammonium compound, and
e) selected carboxylic acid.

Amine.

For preparation of the wood preservative solution according to the present invention an amine is selected from the group consisting of ethanolamine, diethanolamine and triethanolamine.

The best results were achieved, when wood was impregnated with preservative solution consisting of solution where ethanolamine was used as amine source. Almost ten times lowest copper leaching rates were determined when ethanolamine was used compared to diethanolamine or triethanolamine.

Copper Salt.

For preparation of the wood preservative solution according to the present invention a copper salt is selected from the group consisting of copper oxide, copper hydroxide and copper sulphate pent-hydrate.

The best fixation of copper is achieved when copper (II) suphate pent-hydrate ($CuSO_4 \times 5H_2O$) is used as a copper salt.

Copper sulphate is used for wood preservation for long period, but up to our best knowledge, we did not find any report on use of copper sulphate in combination with ethanolamine. During dissolution of this salt, sulphate ion is releasing that decreases the ph value of this solution what results in improved fixation of this respective wood preservative solution.

Boron Salt.

For preparation of the wood preservative solution according to the present invention a boron salt is selected from the group consisting of boric acid, borax and disodium octaborate tetrahydrate ($Na_2B_8O_{13} \times 4H_2O$). These compounds are well known insecticides and fungicides.

The best results were achieved using disodium octaborate tetrahydrate. Combination of this compound with other ingredients resulted in the best performance, best copper fixation and the highest fungicidal effect.

Co-Biocide from the Group of Quaternary Ammonium Compound.

For preparation of the wood preservative solution according to the present invention a quaternary ammonium compound is used as co-biocide. These compounds are used for wood preservation for almost 20 years. In recent years there are even some combination of quaternary ammonium compound and copper available on the market. The most important advantage of this compound is significant fungicidal effect. Additionally, this compounds form new complexes between copper, ethanolamine and quaternary ammonium compound, what results in improved fixation. According to the market availability and biological effectiveness, the alkylbenzyldimethyl ammonium chloride is chosen for preparation of the wood preservative solution according to the present invention.

Carboxylic Acid.

In order to improve fixation of copper in this preservative solution, carboxylic acids are introduced to this aqueous solution as well. For preparation of the wood preservative solution according to the present invention a carboxylic acid is selected from the group consisting of hexanoic acid, octanoic acid and decanoic acid.

The best results were achieved, when octanoic acid was introduced into preservative solution. Octanoic acid has hydrophobic effect. Besides that it has limited fungicidal properties as well. Addition of carboxylic acid significantly decreases copper leaching. Leaching from preservative solution consisting of copper, ethanolamine and octanoic acid is comparable to leaching from copper-chromium treated wood (Table 1).

TABLE 1

| Copper based preservative solution | Copper leached in % |
|---|---|
| Copper (II) sulphate | 45-55% |
| Copper (II) sulphate + ethanolamine | 6-15% |
| Copper (II) sulphate + ethanolamine + disodium octaborate tetrahydrate + quaternary ammonium compound | 4-8% |
| CCB | 0.5-2% |
| Copper (II) sulphate + ethanolamine + disodium octaborate tetrahydrate + quaternary ammonium compound + octanoic acid | 1.1-2% |

Additionally, molar ratio between copper and ethanolamine in preservative solution is important as well. This ratio influences on the price of preservative solution and its resistance against copper leaching. In the most of preservatives the solution molar ratios Cu:amine are lower than 1:12. One of the exemptions is Kuproflorin produced by Regeneracija, Slovenia.

Acceptable copper-amine molar ratios are between 8:1 and 3:1. The best ratio is influenced by copper source used, co-biocides, and other additives. Generally speaking, more additives requires higher copper amine molar ratio. The lowest copper leaching is determined at specimens impregnated with aqueous solution consisting of copper, boron, ethanolamine, quaternary ammonium compound where molar ratio between copper and amine was between 1:5 to 1:6. In solutions where molar ratio was lower than 1:4, copper precipitated.

The most effective composition of preservative solution described in this patent is aqueous solution consisting of ethanolamine, copper (II) sulphate, disodium octaborate tetrahydrate, alkylbenzyldimethyl ammonium chloride, and octanoic acid in the following composition:

a) Ethanolamine (EA) molar ratio between copper and EA should be 1:6,
b) 1% Cu in the form of $CuSO_4 \times 5H_2O$,
c) 0.5% of boron in the form of disodium octaborate tetrahydrate ($Na_2B_8O_{13} \times 4H_2O$),
d) 1% of quaternary ammonium compound in the form of alkylbenzyldimethyl ammonium chloride,
e) octanoic acid molar ratio between Cu:octanoic acid should be 1:1, or expressed as grams of respective ingredients in 1000 g of preservative solution

| | |
|---|---|
| 57.69 g | ethanolamine, |
| 39.32 g | $CuSO_4 \times 5H_2O$, |
| 8.1 g | disodium octaborate tetrahydrate, |
| 10.8 g | alkylbenzyldimethyl ammonium chloride, |
| 11.35 g | octanoic acid. |

Wood, impregnated with preservative solution, prepared according to the present invention, has exhibited sufficient resistance against weathering. Comparable copper leaching rates were determined as at wood impregnated with copper-chromium based solutions. Additionally, wood impregnated with solutions was resistant against most important wood decay fungi. Mass losses of impregnated specimens exposed to white rot fungi (*Trametes versicolor*), brown rot fungi (*Serpula lacrymans, Antrodia vaillantii, Coniophora puteana*) were insignificant (experiments were performed according to standard procedures). Insignificant mass losses were determined after artificially weathering as well. Additionally, this solution protects wood against copper tolerant organisms as well.

Wood impregnated with the solution for wood preservative according to the present invention is resistant against termites (*Kalotermes flavicolis*) as well.

Preparation of Preservative Solution.

Proper amount of ethanolamine is weighted into reaction chamber; afterwards ¼ of water is added, followed by quaternary ammonium compound. When quaternary ammonium compound is dissolved, another ¼ of water is added. Afterwards, copper sulphate and disodium octaborate tetrahydrate is added, followed by ¼ of water. Finally, octanoic acid and last quarter of water is weighted. Preparation of this solution takes place during continuous mixing at room temperature.

What is claimed is:

1. A solution for wood preservation, comprising ethanolamine, copper (II) sulphate pent-hydrate, disodium octaborate tetrahydrate, alkylbenzyldimethyl ammonium chloride, and octanoic acid dissolved in water, wherein 1000 g of aqueous preservative solution comprises 57.69 g ethanolamine, 39.32 g copper (II) sulphate pent-hydrate, 8.1 g disodium octaborate tetrahydrate, 10.8 g alkylbenzyldimethyl ammonium chloride, and 11.35 g octanoic acid dissolved in water.

2. A method for preparing a solution for wood preservation comprising:
   adding ethanolamine into a reaction chamber,
   adding an amount of water,
   adding quaternary ammonium compound to dissolve,
   adding copper sulphate and disodium octaborate tetrahydrate, and
   adding octanoic acid,
   wherein the preparing steps are executed during continuous mixing at room temperature.

3. A method for preparing a solution for wood preservation according to claim 2, wherein said adding steps occur in the order:
   a) adding the ethanolamine into reaction chamber,
   b) adding the water,
   c) adding the quaternary ammonium compound to dissolve,
   d) adding the water,
   e) adding the copper sulphate and disodium octaborate tetrahydrate,
   f) adding the water,
   g) adding the octanoic acid, and
   h) adding the water.

* * * * *